(12) United States Patent
Yoo et al.

(10) Patent No.: US 9,061,369 B2
(45) Date of Patent: Jun. 23, 2015

(54) METHOD FOR REAL-TIME OPTICAL DIAGNOSTICS IN LASER ABLATION AND LASER PROCESSING OF LAYERED AND STRUCTURED MATERIALS

(75) Inventors: Jong Hyun Yoo, Milpitas, CA (US); Alexander A. Bol'shakov, Los Altos, CA (US)

(73) Assignee: Applied Spectra, Inc., Fremont, CA (US)

(*) Notice: Subject to any disclaimer, the term of this patent is extended or adjusted under 35 U.S.C. 154(b) by 565 days.

(21) Appl. No.: 12/939,095

(22) Filed: Nov. 3, 2010

(65) Prior Publication Data
US 2011/0100967 A1     May 5, 2011

Related U.S. Application Data

(60) Provisional application No. 61/257,802, filed on Nov. 3, 2009.

(51) Int. Cl.
| | | |
|---|---|---|
| B23K 26/03 | (2006.01) | |
| G01N 27/00 | (2006.01) | |
| B23K 26/06 | (2014.01) | |
| B23K 26/38 | (2014.01) | |

(52) U.S. Cl.
CPC .............. *B23K 26/032* (2013.01); *G01N 27/00* (2013.01); *B23K 26/0635* (2013.01); *B23K 26/38* (2013.01)

(58) Field of Classification Search
CPC ............. B23K 26/032; B23K 26/0635; B23K 26/4085; B23K 26/409; G01N 27/18
USPC ................. 219/121.69, 121.83; 356/318, 317
See application file for complete search history.

(56) References Cited

U.S. PATENT DOCUMENTS

| | | | | |
|---|---|---|---|---|
| 5,013,917 A | * | 5/1991 | Ulich | 250/330 |
| 5,063,280 A | * | 11/1991 | Inagawa et al. | 219/121.71 |
| 5,592,283 A | * | 1/1997 | Flesher et al. | 356/72 |
| 5,656,186 A | * | 8/1997 | Mourou et al. | 219/121.69 |
| 5,847,825 A | * | 12/1998 | Alexander | 356/318 |
| 6,526,327 B2 | * | 2/2003 | Kar et al. | 700/166 |
| 6,787,734 B2 | * | 9/2004 | Liu | 219/121.71 |
| 7,060,932 B2 | * | 6/2006 | Denney et al. | 219/121.78 |

(Continued)

FOREIGN PATENT DOCUMENTS

| | | | |
|---|---|---|---|
| DE | 10060407 A1 | * | 6/2002 |
| EP | 544398 A1 | * | 6/1993 |
| WO | WO-02/29853 A2 | * | 4/2002 |

OTHER PUBLICATIONS

Machine translation of DE 10060407, Sep. 2012.*

(Continued)

*Primary Examiner* — Geoffrey S Evans
(74) *Attorney, Agent, or Firm* — Microtechnology Law & Analysis; Daniel L. Flamm

(57) ABSTRACT

A method for real-time optical diagnostics in laser ablation and laser processing of layered or structured materials or material structures. Diagnostics is provided during laser ablation that is utilized regularly in laser processing and/or chemical analysis of structured materials, by means of measuring optical emission generated as a result of the pulsed laser-material interaction in real time. The method can involve a single-layer-film or a stack of multiple layers or a structure of different domains. The method is particularly beneficial in fabrication of thin-film structures, such as photovoltaic and electronic devices or circuits of devices.

24 Claims, 5 Drawing Sheets

(56) References Cited

U.S. PATENT DOCUMENTS

| | | |
|---|---|---|
| 7,151,609 B2 | 12/2006 | Chalmers et al. |
| 7,240,839 B2 | 7/2007 | Jung et al. |
| 7,363,180 B2 | 4/2008 | Swaringen et al. |
| 2003/0047544 A1* | 3/2003 | De Steur et al. ......... 219/121.71 |
| 2003/0231306 A1* | 12/2003 | Gornushkin et al. ......... 356/318 |
| 2005/0194365 A1* | 9/2005 | Li ............................ 219/121.68 |
| 2007/0008526 A1* | 1/2007 | Buczkowski ................. 356/318 |
| 2007/0046934 A1 | 3/2007 | Roy |
| 2007/0296966 A1 | 12/2007 | Benicewicz et al. |
| 2008/0037005 A1 | 2/2008 | Bareket et al. |
| 2008/0070327 A1 | 3/2008 | Ogasawara et al. |
| 2009/0091745 A1* | 4/2009 | Levesque et al. ............... 356/73 |
| 2009/0127233 A1* | 5/2009 | Asano et al. ............... 219/121.7 |
| 2009/0290151 A1* | 11/2009 | Agrawal et al. ............ 356/318 |
| 2010/0197116 A1* | 8/2010 | Shah et al. ..................... 438/463 |
| 2011/0017715 A1* | 1/2011 | Marcus et al. ........... 219/121.71 |
| 2012/0206722 A1* | 8/2012 | Grigoropoulos et al. ..... 356/318 |

OTHER PUBLICATIONS

Tong et al., "Real-time control of ultrafast laser micromachining by laser-induced breakdown spectroscopy", Mar. 2004, Applied Optics, vol. 43, No. 9, pp. 1971-1980.*

Siegel et al., "High Spatial resolution in laser-induced breakdown spectrscopy of expanding plasmas", Jun. 2005, Elsevier Spectrochimica Acta Part B vol. 60, pp. 915-919.*

Semerok, "LIBS with Ultrashort Laser Pulses: Fundamental and Analytical Aspects", Jun. 14, 2009, ISTN/CEA Sacaly France, slides 1-49.*

International Search Report and Written Opinion of the International Searching Authority, mailed Dec. 30, 2010, for Application No. PCT/US2010/055327, 9 pages.

* cited by examiner

METHOD FOR REAL-TIME OPTICAL DIAGNOSTICS IN LASER ABLATION AND LASER PROCESSING OF LAYERED AND STRUCTURED MATERIALS

CROSS-REFERENCE TO RELATED APPLICATIONS

This application claims priority to U.S. Provisional Application Ser. No. 61/257,802, filed Nov. 3, 2009, entitled "METHOD TO IMPLEMENT ENDPOINT SENSOR AND TO PERFORM SENSITIVE CHEMICAL ANALYSIS DURING LASER SCRIBING, DRILLING AND CUTTING," which is hereby incorporated by reference in its entirety as if set forth herein.

FIELD OF THE INVENTION

The present invention relates to a method of real-time optical diagnostics in laser ablation and laser processing of single-layered, multi-layered, coated, composite, granulated or otherwise structured materials or structures. It has particular utility for industrial laser processes applied during fabrication of thin-film structures, such as photovoltaic and electronic devices.

BACKGROUND OF THE INVENTION

Many microelectronic devices are made of layered thin film structures with a plurality of interconnected functional layers that are conductive, semiconductive, insulating, doped, or protective. One example includes photovoltaic conversion devices, such as thin-film solar cells. Processes of manufacturing of such devices often involve multiple steps of laser drilling, cutting, scribing, and patterning of the layers of different materials including antireflection optical coatings. In particular, laser scribing is becoming a dominant technique for thin-film solar cell fabrication. However, an energetic laser beam can also inadvertently damage the underlying layer. It is difficult to recognize the point at which a laser action must be discontinued to ensure a complete removal of the desired layer(s), but at the same time prevent any damage to the underlying structure.

Fabrication of micro-electro-mechanical systems (MEMS) demands comparable processing of various layers and structures made of foils, semiconductors, ceramics, plastic masks, and metal stencils. In addition, many integrated circuits are encapsulated in plastic packages that have external contacts for electrically interfacing with the circuit. Similar plastic coatings are used on printed circuit boards. Sometimes such circuits fail. Commonly, manufacturers of such devices will analyze failed devices to understand the failure mechanism to determine whether a design change is warranted.

For conventional failure analysis of integrated circuits, a practitioner uses a wet etch to remove the plastic encapsulation. The etch is an acid that is selected to attack the plastic, but that is benign to the circuit. In this way, the plastic is removed while leaving the circuit with no further damage resulting from the plastic removal. Unfortunately, practitioners find that the wet etch technique is excessively time consuming and seek a more efficient plastic removal technique.

A laser pulse can attack and remove substantially any material on which it impinges. Because of the high temperature created by laser-material interaction, part of the ejected material will emit light that is characteristic of the ablated material. A laser can be scanned in a two-dimensional pattern across a surface to ablate the entire surface (e.g., the surface of a plastic integrated circuit package). During this process, conventional instrumentation cannot distinguish between the plastic and the underlying integrated circuit. Thus, a conventional scanning of a laser used to strip the plastic package or coating will either result in not exposing the integrated circuit or damaging the circuit, with neither such result providing the desired outcome.

Several diagnostics and metrology techniques are commonly used to characterize photovoltaic devices, including reflectometry, ellipsometry, x-ray fluorescence, x-ray reflectance, energy dispersive x-ray spectroscopy, secondary ion mass spectrometry, inductively coupled plasma mass spectroscopy, laser ablation inductively coupled plasma mass spectroscopy, scanning electron microscopy, transmission electron microscopy, scanning tunneling microscopy, atomic force microscopy, and other techniques. However, these established techniques are not practical for real-time diagnostic measurements during rapid laser processing of structured materials. X-ray techniques require long acquisition times. Mass spectrometry and electron microscopy require ultra-high vacuum. Most often used ellipsometry and reflectometry cannot measure opaque films and both are indirect techniques based on computational models with a large number of floating parameters. If the film properties deviate in such a way that the assumptions of the model are not valid, these techniques yield wrong results.

SUMMARY OF THE INVENTION

Optical emission measurements are well suited for in-situ metrology and diagnostics during pulsed laser processing of materials in real time. Optical emission can provide excellent specificity to chemical composition of the processed material and can be measured very fast. Optical measurements do not require vacuum and can be implemented in a contact-less configuration from a stand-off distance. Accordingly, it is desirable to have a method of optical diagnostics that can be applied in-situ during laser ablation and laser processing in real time. This method can be fully automated and enables high efficiency and throughput in manufacturing at the best attainable precision and minimization of damage to the products.

By combining a scannable processing laser with an optical emission detection system and a control system, used as an optical diagnostics system, the laser can form blind holes or can be scanned across the multilayered electronic structures to remove the desired layers without causing damage to the underlying layers. An optical detection and analysis system can distinguish in real time between the material to be removed from the underlying materials. As soon as the material from the underlying layer is detected in the laser ablation plume by the optical diagnostics system, either the laser is stopped or the laser's power is reduced to prevent damage of the underlying layer.

One aspect of the present invention is for a method of performing real-time optical diagnostics of a single film or of multilayered or structured materials or material structures during laser ablation or laser processing of such materials or structures. The method comprises measuring the optical spectral emission from the laser-ejected material and then using this obtained information to identify, at least partially, the chemical composition of the processed material. A change in chemical composition indicates that laser ablation has reached a different layer or domain of the structured material. These diagnostic techniques can be used in-situ to monitor specific chemical information during material processing to control or examine desired depth or lateral length of the laser processing. The method can alternatively involve material analysis and diagnostics performed after or without any connection to the phase of material processing. The present invention can be used to determine the composition of the primary chemical constituents or trace elements present in each layer or domain of a material structure during laser processing (drilling, scribing, multiple pulse laser ablation of structured materials) in an addition to the in-situ monitoring or diagnostic capability to control the processing due to the finding of different chemical information available from different layers or domains in the structure.

A focused laser beam is directed at a processed material to initiate ablation resulting in a plume of excited ejected material that emits electromagnetic radiation, such as light. Optical emission from this plume is collected and analyzed using a spectrometer. The optical spectrum provides a signature of the chemical species present in the sample. Spectral data analysis provides at least partially the chemical composition and relative abundance information.

In one illustrative embodiment, optical emission is collected with at least one lens and coupled via a fiberoptic cable to a measuring device, preferably an optical spectrograph fitted with a CCD or ICCD camera, which digitizes the spectral data for further computational analysis in real time. In this fashion, the present invention enables the practitioners to realize the disclosed method of optical diagnostics from a stand-off distance without direct contact with the ablated material. Therefore, no physical disturbance or interference with the material processing is required to implement the provided optical diagnostic method. The stand-off distance will preferably be small in order to facilitate efficient collection of the optical emission. However, the stand-off distance can be increased to several meters or tens of meters, if so desired.

In another illustrative embodiment, a CCD or ICCD camera is synchronized with the individual laser ablation pulses in such a way that optical emission is measured with an appropriate delay after a laser pulse and only during a gated period of time. The delay and the gate width are optimized to enhance useful spectral features, while concurrently decreasing continuum background in laser-generated optical spectra. When a pulsed laser with a high repetition rate is used for material ablation, the fast on-chip accumulation of spectral data in the pixels of the CCD or ICCD camera integrated over multiple laser pulses can be preferred in order to increase the signal-to-noise ratio. Alternatively, spectral data from each individual pulse can be measured to detect a change of chemical composition of the material in a technique often referred to as "end-point detection."

Although the present invention is particularly useful in end-point detection to detect a change in chemical composition of the ablated material, it is also useful in the detection and diagnostics of the primary or trace level chemical constituents. Bulk and trace level chemical composition often influences the efficiency of different solar cells that include copper indium gallium de-selenide (CIGS), CdTe, amorphous Si, crystalline Si, organic PV, III-V compounds, and hybrid amorphous/multicrystalline solar devices. While laser processing is performed on one or more layers of thin films, the present invention provides the unique capability to monitor the bulk and trace level chemical constituents in the thin film layer(s).

In accordance with another aspect of the present invention, computational statistical analysis of digital spectral data can be further implemented to identify and characterize the ablated material on the basis of the measured spectra. Aforesaid statistical analysis is often referred to as "chemometric analysis" or "chemometrics." In the present invention, the chemometric algorithms will compare a real-time measured spectrum to the spectra stored in a reference database in memory of a system computer. This method allows practitioners to identify, discriminate and characterize the ablated materials in a real-time automated mode of operation. This method can be used to discriminate between materials of similar elemental composition, but of different molecular structure. Some physical properties of the materials, such as reflectance or density, and certain crystallographic structures can also be discriminated in many cases. Accordingly, material compositional and structural consistency or deviations from thereof during the process can be monitored in real time.

It will be appreciated that functional material structures are often three-dimensional. For example, the upper surfaces of microelectronic devices, integrated circuits, photovoltaic cells, and micromechanical systems are typically not planar. Moreover, electrical contacts such as bond wires or flip chip solder bumps are typically raised above the surface of the electronic devices. The control system associated with the present invention can include a memory and a raster locator. The laser can be scanned over the entire surface of the electronic device until a first location is detected and stored for which material of the layer of interest is detected. On a next scan, the laser can be toggled off for that location. In a removal of an overlaid plastic packaging cover, for example, the scanning of the laser can continue until an entire upper surface of the device is exposed, yet remains undamaged by the removal of the plastic package.

In accordance with yet another aspect of the present invention, a method of performing real-time optical diagnostics of a target during laser ablation of the target is provided. The method comprises focusing a laser beam of a laser on the target. The target can be a material or a structure. At least one location of the target is ablated using a pulsed laser beam to cause at least a fraction of material ejected from the ablated location of the target to emit plurality of photons with wavelengths specific to the ablated material. Optical emission spectral information of the emitted photons is measured using a measuring device. At least part of the chemical or physical characteristics of the ablated material is identified using the optical emission spectral information.

In accordance with yet another aspect of the present invention, a method of performing real-time optical diagnostics or analysis of at least one layer or at least one domain of structured material during laser ablation or laser processing of the material or structure is provided. The method comprises focusing the laser beam on or slightly below the surface of the material or structure, and ablating at least one location of the material using a pulsed laser beam to cause at least a fraction of the ejected material to emit a plurality of photons with wavelengths specific to the ablated material. At least one segment of the optical spectrum of the emitted photons is measured in accordance with their spectral wavelength using a measuring device. At least one kind of chemical species (ionized or neutral, atomic or molecular) in the ejected material is identified using obtained spectral information. It is then determined whether there has been a change in chemical composition of the ablated material from two or more laser pulses directed either in: a) the same location, and thus ejecting the material from at least two consecutive depth points; or b) at least in two different locations on the surface of the ablated material. At least one of the following material characteristics is inferred: a) presence or absence of at least one kind of chemical species; b) depth of at least one layer; or c)

at least one boundary between at least two surface domains of different chemical composition.

In some embodiments, the ablating comprises ejecting, vaporizing or pulverizing a small portion of material using the pulsed laser beam of sufficient energy for the purpose of laser processing of the layered, coated, composite, granulated or otherwise structured material or structure in processes such as micromachining, cutting, stripping, blanking, scribing, drilling, boring, piercing, marking, signing, engraving, trimming, texturing, welding, soldering, patterning, measuring, scanning, profiling, and the like. In some embodiments, the ablating further comprises ablating using a pulsed laser with a high rate of pulse repetition, preferably in a kilohertz range up to a megahertz range.

In some embodiments, the measuring comprises measuring spectral intensities using optical spectroscopy in a broad sense that involves electromagnetic radiation, which can be microwave, terahertz, infrared, visible, ultraviolet, or x-ray radiation. In some embodiments, the measuring further comprises measuring using a spectroscopic apparatus which collects and detects electromagnetic radiation such as light from a stand-off distance without direct contact with the ablated material. In some embodiments, the measuring further comprises measuring using accumulation of the spectral data with a coupled charge device (CCD) or intensified CCD (ICCD) camera over multiple laser pulses. In some embodiments, the measuring further comprises measuring using fast-gated direct accumulation of the spectral data on the chip of an ICCD camera over multiple laser pulses, wherein gated on-chip accumulation facilitates enhancing at least one useful spectral feature while concurrently decreasing continuum background in laser-generated optical spectra.

In some embodiments, a focus point of the ablating laser beam is moved vertically or horizontally or in both directions relative to the surface of the ablated material using beam steering techniques controlled by a system computer. In some embodiments, the ablated material is moved vertically or horizontally or in both directions using a stage coupled thereto and controlled by a system computer. In some embodiments, the ablating laser is moved vertically or horizontally or in both directions relative to the ablated material using a stage coupled to the laser and controlled by a system computer.

In some embodiments, the method further comprises quantifying absolute or relative intensity of at least one spectral feature of at least one kind of chemical species, wherein the quantifying comprises obtaining, converting, and storing relevant digital data using a system computer. In some embodiments, the method further comprises distinguishing between either: a) at least two vertical layers, or b) at least two horizontal domains in compositional structure of the ablated material in real time. In some embodiments, the method further comprises calibrating intensity of at least one spectral feature against compositional concentration of the corresponding chemical species in the ablated material.

In some embodiments, the method further comprises computational statistical transformation of digital spectral data using chemometric algorithms to identify and characterize the ablated material using a system computer to compare and discriminate the spectral patterns. In some embodiments, the method further comprises monitoring at least one kind of bulk or trace chemical species in the ablated material during the process in real time, wherein the chemical species can be in atomic or molecular form, can be a desired compositional component, or can be an undesired impurity or contaminant in the material or on the surface of the same. In some embodiments, the method further comprises implementing so-called damageless laser ablation of upper coatings on electronic, photovoltaic, micromechanical, and similar structures to ensure a stable ablation quality and to preserve the underlying wafer from damage. In some embodiments, the coatings comprise thin layers of any type, including metallic, dielectric, plastic, organic, which are functional or protective. In some embodiments, the wafer comprises a substrate of any type, including silicon, gallium arsenide, gallium phosphate, indium phosphate, germanium, sapphire, graphite, ceramic, quartz, glass, pyrex, polymers, biological materials, and others.

In some embodiments, the method further comprises implementing laser drilling through wafer substrates or overlaid structures to ensure a process stability and consistent quality of the product. In some embodiments, the method further comprises monitoring at least one type of the ablated material for compositional consistency or deviations from thereof during the process in real time. In some embodiments, the method further comprises implementing end-point detection to be used as a feedback for a system computer to terminate the laser processing of the material or structure. In some embodiments, the method further comprises identifying at least one doped area or a gradient of a dopant in the material.

DETAILED DESCRIPTION OF THE INVENTION

Figure 1:
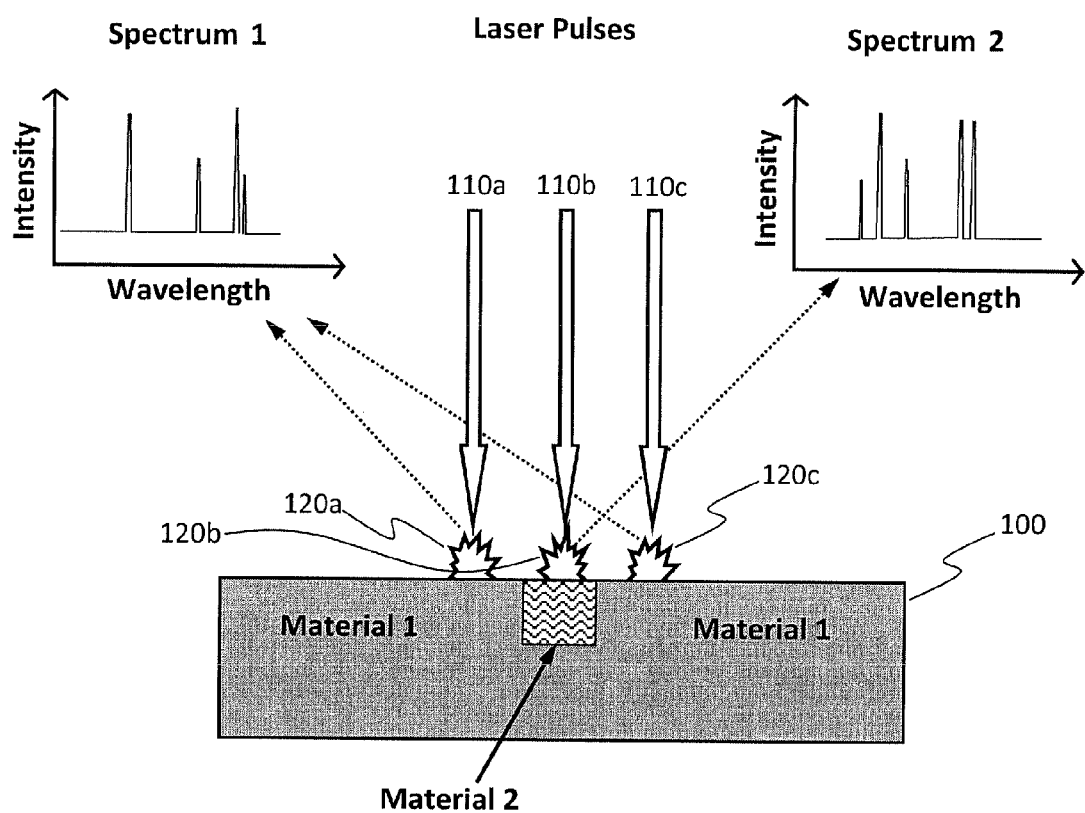
FIG. 1 illustrates schematically the laser ablation processing across a structure that comprises of two materials.

The following description is presented to enable one of ordinary skill in the art to make and use the invention and is provided in the context of a patent application and its requirements. Various modifications to the described embodiments will be readily apparent to those skilled in the art after reading this document and the generic principles herein may be applied to other embodiments. Thus, the present invention is not intended to be limited to the embodiment shown but is to be accorded the widest scope consistent with the principles and features described herein.

Various aspects of the disclosure may be described through the use of flowcharts. Often, a single instance of an aspect of the present disclosure may be shown. As is appreciated by those of ordinary skill in the art, however, the protocols, processes, and procedures described herein may be repeated continuously or as often as necessary to satisfy the needs described herein. Additionally, it is contemplated that certain method steps of the invention can be performed in alternative sequences to those disclosed in the flowcharts. Accordingly, the scope of the claims should not be limited to any specific order of method steps unless the order is required by the language of the claims.

In the following detailed description of the embodiments and examples, the details and alternatives are set forth for the purpose of explanation. However, one of ordinary skill in the art will realize that the invention can be practiced without the use of these specific details. In other instances, known techniques and devices are referenced without full elucidation in order not to obscure the description of the invention with unnecessary detail.

Unless otherwise specified, all technical and scientific terms used herein have the same meaning as commonly understood by one of ordinary skill in the art to which this invention belongs. Techniques, technologies, structures, and materials suitable for the present invention are described herein, although similar or equivalent materials and techniques can generally be used in practice or testing of the present invention.

The present invention provides a method of optical diagnostics in laser ablation and laser processing of structured materials or structures of materials in real time and without any intrusion or direct physical contact to the processed material. Diagnostics is provided during laser ablation that is utilized in laser processing and/or chemical analysis of structured materials, by means of measuring optical emission generated as a result of the pulsed laser-material interaction in real time. The method is particularly beneficial in fabrication of thin-film structures, such as photovoltaic and electronic devices or circuits of such devices. The method of optical diagnostics disclosed herein is also germane to multiple other applications related to processing of thin-films, multilayered stacks, and coatings, including fabrication of optical devices, micromechanical devices, protective coatings, paint layers, pharmaceutical coatings, advanced and modified surfaces of various materials.

The method includes, in an illustrative embodiment, monitoring and analyzing optical emission spectra during laser processing of materials as an in-situ diagnostic technique. Ejection of luminous plumes of the material from the material surface is a side-effect of pulsed laser ablation of the processed materials or structures, such as photovoltaic solar cells. Optical emission from these plumes can be analyzed in real time. Accordingly, optical emission measurement during laser processing of materials can be used as non-intrusive in-situ metrology for process control and feedback. Spatial resolution of the material sampling achievable with laser ablation is on the order of ~10 nanometers in depth drilling or profiling, and <1 micrometer in lateral directions. Therefore, accurate three-dimensional surface metrology and diagnostics can be realized with this method to improve quality and yield of the products, and thereby to decrease manufacturing costs.

Referring to FIG. 1, in an illustrative embodiment, the provided schematic diagram displays how consecutive laser pulses perform spaced ablation of the structured material 100, which in this example comprises for simplicity only two constituents, namely Material 1 and Material 2. Each laser pulse 110a, 110b, 110c generates a luminous plume of ejected material 120a, 120b, 120c, respectively. Optical emission from these plumes is collected by an optical system, and is then measured and analyzed with a measuring device, such as an optical spectrograph equipped with a CCD or ICCD camera. The obtained spectral information is forwarded to a system computer for computational chemometric treatment of data to characterize and discriminate between the two different constituents of the structured material shown in this example. Recorded optical emission spectra from each consecutive pulse are characteristic of the ablated material; distinct materials will have distinctively different spectra. This example is relevant to many different processes, such as scribing, cutting, stripping, micromachining, marking, signing, engraving, trimming, texturing, patterning, measuring, scanning, profiling, and others. Although FIG. 1 shows laser pulses 100a, 100b, 100c directed in three different lateral locations on the surface of the structured material 100, it is contemplated that the laser pulses could additionally or alternatively be directed in the same lateral location, thus ejecting the ablated material from at least two consecutive depth points, with each depth point being successively deeper.

Figure 2:
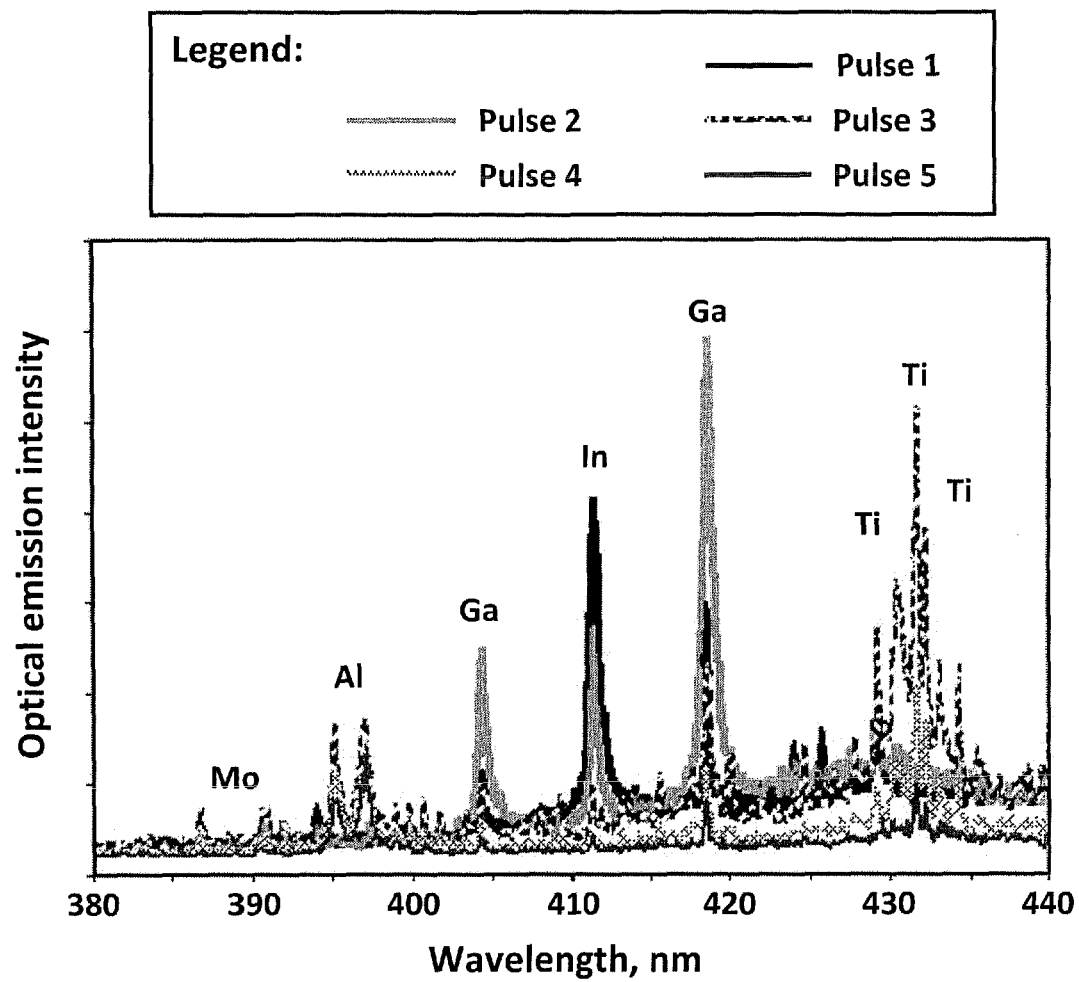
FIG. 2 illustrates a plot of spectral information from successive laser ablation plumes in accordance with the principles of the present invention.

FIG. 2, shows an illustrative embodiment. The presented spectra demonstrate how optical emission from successive laser ablation plumes during laser drilling can be used to obtain chemical information and identify consecutive layers of the film stack structure of an exemplary solar cell based on copper indium gallium di-selenide (CIGS). In this example, each successive laser pulse is fired into the same spot, forming a crater deeper and deeper in the stack structure. Accordingly, the recorded series of spectra corresponds to the consecutive layers of the stack. The CIGS photovoltaic structure used in this example had a film stack of CIGS, Mo, Ti, and Al layers, from top to bottom. The displayed series of spectra corresponds to the consecutive layers of the structure. The recorded optical spectra indicates presence of Al, Ga, In, Mo, and Ti in different layers. Using this information, their chemical composition and homogeneity, and the thickness of the layers in some embodiments, can be determined and monitored in real time.

Figure 3:
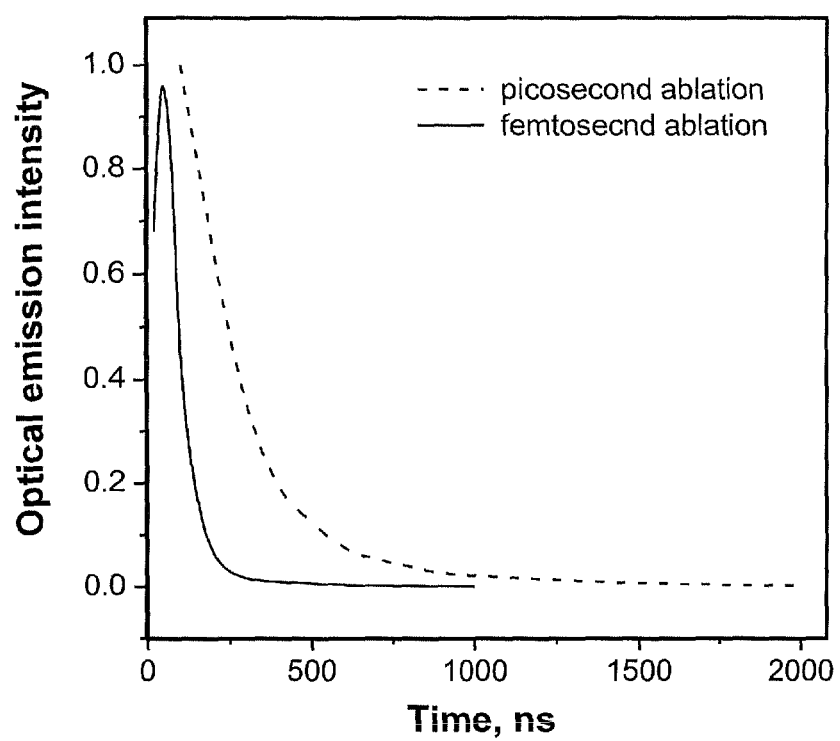
FIG. 3 illustrates the lifetime of the optical emission generated by ablation with picosecond and femtosecond lasers in accordance with the principles of the present invention.

FIG. 3 illustrates the lifetime of the optical emission generated by ablation with picosecond and femtosecond lasers. In an illustrative embodiment, the presented chart reveals temporal behavior of the optical emission generated by ablation of copper with picosecond and femtosecond lasers. In industrial processing of materials, pulsed lasers with high-repetition rates are commonly utilized. Typically, energy output of such lasers is limited to microjoule (μJ) or low millijoule (mJ) levels per pulse. In some embodiments, the present invention employs a laser having an energy output between approximately 0.5 μJ and approximately 1 mJ. In this example, lifetime of the optical emission is shorter than 1 microsecond, as indicated in the chart. Accordingly, the optimal delay of gated data acquisition is less than 1 microsecond in the processes with picosecond and femtosecond lasers. In some embodiments, the high-repetition rate nanosecond lasers are used for drilling of vias and scribing of solar cells and semiconductor processing; such lasers also have typical output energy of approximately 1 mJ or less. Accordingly, the optimal delay of gated data acquisition is also less than 1 microsecond in the processes with nanosecond lasers. This is in contrast to long-lived optical emission (several microseconds up to approximately 1 millisecond) that can be generated by ablation with low-repetition lasers, which yield high energy pulses on the order of 10 mJ per pulse or higher.

Therefore, short delays and fast gating is required for optimal detection of the optical emission during typical industrial processing of materials. In an illustrative embodiment, a CCD or ICCD camera is used for spectral registration. Such detectors can provide on-chip accumulation to increase signal-to-noise ratio of the recorded spectra, while making possible very fast gating. On-chip accumulation refers to adding up multiple exposures to integrate many photons in the pixels on a CCD detector chip before they are read out. It is possible to transfer the integrated charge quickly under the CCD storage areas.

Figure 4:
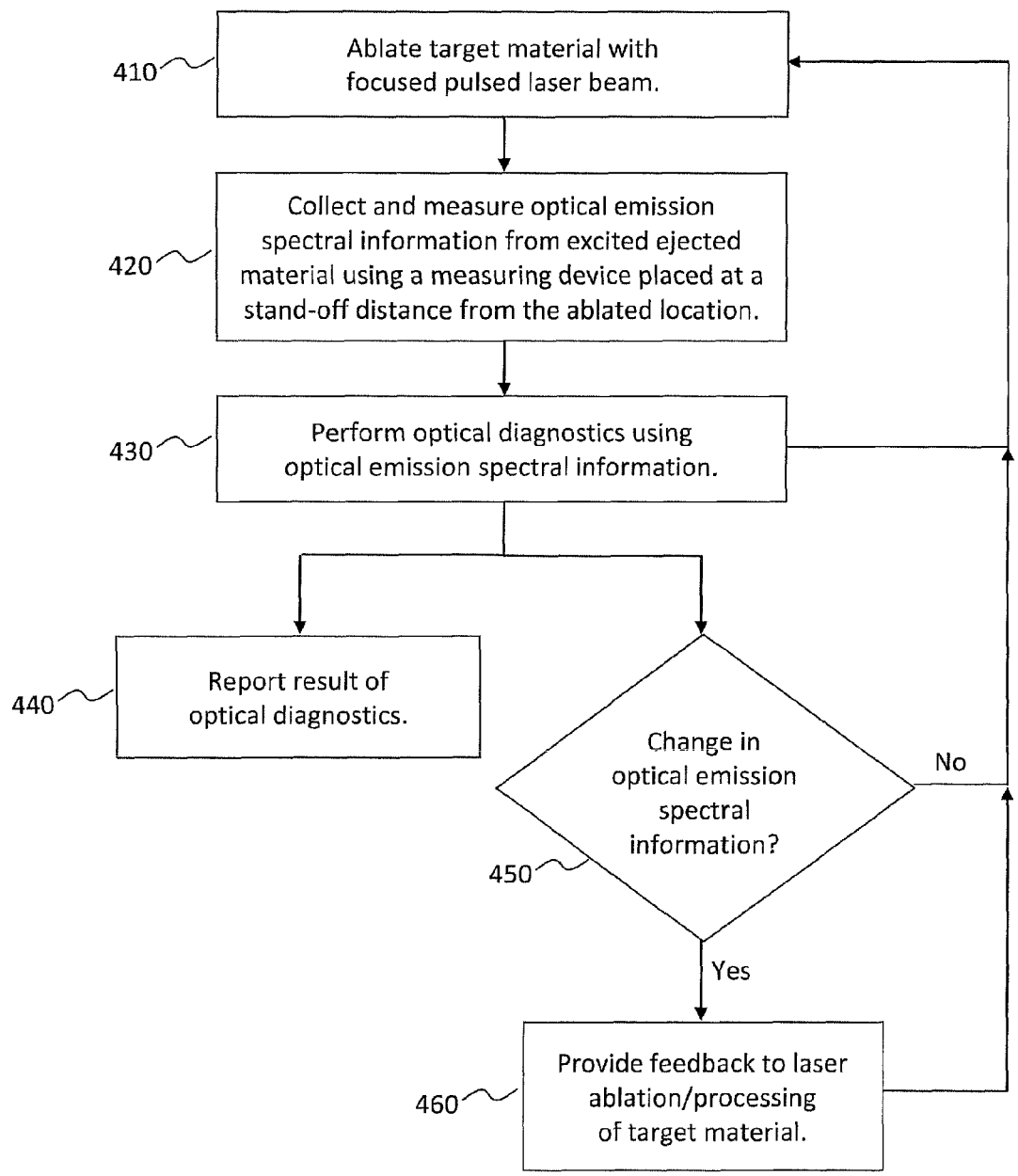
FIG. 4 illustrates one embodiment of a process flow diagram for a method of real-time optical diagnostics in laser ablation and processing of structured materials in accordance with the principles of the present invention.

FIG. 4 illustrates one embodiment of a process flow diagram for a method 400 of real-time optical diagnostics in laser ablation and processing of structured materials in accordance with the principles of the present invention. At step 410, a target, such as a material or a structured material or a structure of materials, is ablated with a focused pulsed laser beam, thereby generating a plume of luminous ejected material. At step 420, optical emission spectral information is collected and measured from the excited ejected material using a measuring device situated at a stand-off distance from the spot of material ablation. At step 430, optical diagnostics are performed using the optical emission spectral information. In some embodiments, the optical diagnostics are used to determine the material composition of the primary chemical constituents or trace elements present in one or more layers or domains, or other characteristics of the target. In some embodiments, the optical diagnostics are used to identify the ablated material. The results of the optical diagnostics, such as the identification of the ablated material, can then be reported at step 440.

Additionally, or alternatively, multiple successive laser pulses can be used to ablate the target material or structure, to collect, measure, and analyze the spectra of the target material. After two or more repetitions of these steps, it can be determined at step 450 whether or not there has been a change in the optical emission spectrum obtained from two or more consecutive laser pulses that successively ablate two or more layers or domains of the target. In some embodiments, this determination is made by a computer. If there has not been a change, then the process continues on, repeating the ablation, collection, measurement, and analysis at step 410. If there has been a change, then the process provides feedback to the laser ablation processing of the target at step 460. For example, in some embodiments, the system computer instructs the laser to stop. In some embodiments, the system computer instructs the laser to reduce its power before repeating the ablation, collection, measurement, and analysis at step 410. Accordingly, a technique of end-point detection can be implemented in this way.

In the following illustrative examples of laser processing of materials, the disclosed method of real-time optical diagnostics can be applied during ablation processes:
(a) to pattern or remove layers;
(b) to selectively remove regions or paths;
(c) to drill non-conductive pathways;
(d) to remove selective portions of the layered material;
(e) to define electrode patterns;
(f) to allow the edge definition of the source/drain electrodes and data lines;
(g) to isolate doped areas by cutting or drilling an opening between two regions; and
(h) to groove the surface for antireflective coatings.

Laser processing of materials is commonly exploited nowadays instead of conventional lithography to decrease complexity of the fabrication process. In other examples, laser processing replaces mechanical cutting or drilling to precisely and directly micromachine the structures.

In the following illustrative examples, the disclosed method of real-time optical diagnostics can be applied as the end-point detection or other process monitoring technique during laser scribing, laser drilling, laser cutting, and laser stripping of materials with particular utility to fabrication of photovoltaic solar cells, both thick-film and thin-film solar cells, plurality of photoelectric devices, transistor arrays, photomasks, wafers, lithium or other batteries, etc.:
(a) to divide conductive coatings into isolated stripes on a substrate (glass, steel, plastic, etc);
(b) to pattern vias that can be used to connect the top electrode to the bottom electrode;
(c) to selectively remove regions or paths in any layered products to produce designed distributions, shapes, patterns, etc.;
(d) to detect possible impurities in-situ, while scribing to ensure chemical consistency of the films;
(e) to groove the top and bottom surfaces of the solar cell to enhance the antireflective properties and to improve resistance to radiation of the cell surface by increasing the lifetime of minority carriers;
(f) to form vias in a wafer-level-processed stacked memory packaging (WSP) to fabricate the dynamic random access memory (DRAM) chips;
(g) to drill for direct connection between non-volatile NAND stacked memory devices (logical NOT+AND operator);
(h) to drill for multi-chip bonding and interconnect;
(i) to drill via holes to reduce top contact shading in solar cells to provide holes through the substrate as in metal-wrap-through (MWT) and emitter-wrap-through (EWT) solar cells;
(j) to cut the top thin n-type layer to isolate the individual solar cells to complete the fabrication;
(k) to strip a plastic package from an integrated circuit;
(l) to strip a photoresist layer;
(m) to remove organic, polymer or other layers during the manufacture of semiconductor devices, wafers, thin-film transistors, and thin film transistor liquid crystal displays (TFT-LCD), etc.;
(n) to provide real-time monitoring, particularly to provide surface and depth chemical maps of coatings, coated substrates, and layered stacks; and
(o) to provide chip-level chemical analysis of thin-film layers and/or packaging structures.

Figure 5:
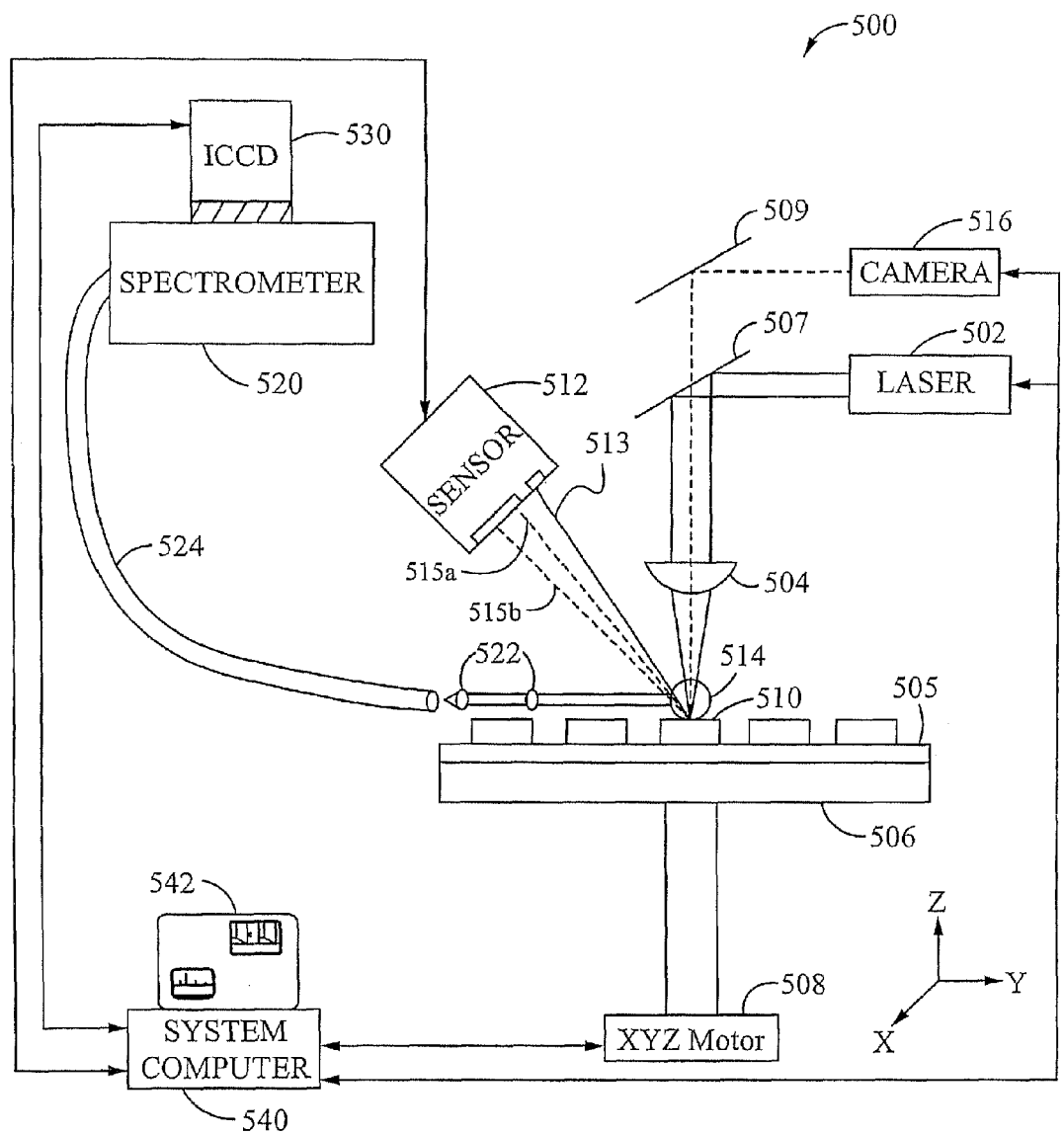
FIG. 5 illustrates one embodiment of a laser ablation apparatus in accordance with the principles of the present invention.

FIG. 5 illustrates a schematic overview of a laser ablation processing apparatus 500 in accordance with one embodiment of the present invention. The apparatus 500 generally includes a pulse laser 502, a stage 506, a position sensor 512, a spectrometer 520, and a system computer 540. The apparatus 500 is configured to generate laser pulses from the pulse laser 502. The laser pulses are focused onto a processed structure 505 with a lens 504 to produce a plume 514 of the processed structure 505 at a target location 510. In some embodiments, the position sensor 512 is communicatively coupled with the system computer 540 for sending a displacement error signal to automatically correct positioning of the stage 506 during an ablating process as described further below. The apparatus 500 can include a system frame for housing the various components described herein. The system frame can include an air filter for filtering contaminants produced during the ablating process.

In some embodiments, the pulse laser 502 comprises a neodymium doped yttrium aluminum garnet (Nd:YAG) laser for generating energy in the near infrared region of the electromagnetic spectrum with a wavelength of 1064 nm. In some embodiments, the pulse duration can be approximately 4 ns for generating a laser beam focused on the ablation impact point. In some embodiments, the laser 502 has a repetition rate of between 0.5 kHz and 1 MHz. In some embodiments, the laser 502 has a repetition rate of approximately 10 Hz. In some embodiments, the laser 502 has a repetition rate of lower than 10 Hz. However, it is contemplated that the present invention can employ other repetition rates. Alternatively, the pulse duration can vary from tens of femtoseconds to hundreds of nanoseconds. In another embodiment, the pulse duration can be shortened to ultra short femtoseconds. In some embodiments, the lens 504 comprises an objective lens used to focus the laser beam on a surface of the target location 510. The laser beam can be focused to a spot size of less than 1 micrometer. Alternatively, the laser beam can be focused to a spot size of approximately 10-500 micrometers on the target location 510 in some embodiments.

In some embodiments, a dichroic mirror 507 is used for directing the laser beam toward the target location 510, and a mirror 509 allows viewing of the target location 510 using a video camera 516. The stage 506 includes an attached array of 'x-y-z' motors 508 for providing translation of the stage 506 in a three dimensional space. The x-y-z motors can comprise suitable stepper motors as known by a person of skill in the art.

The position sensor 512 preferably comprises a laser triangulation sensor. The position sensor 512 preferably uses the principle of triangulation to determine changes in height of the stage 506 and the associated processed structure 505. Triangulation occurs when the position sensor 512 emits a triangulation laser 513 that is focused on the target location and a first reflection 515a is sensed by a photodetector within the position sensor 512. A change in height of the target location 510 causes a displacement in the triangulation laser 513 to produce a second reflection 515b and a displacement signal generated by the position sensor 512 is communicated to a system computer 540. The system computer 540 provides positioning information to maintain an optimum height of the processed structure. The position sensor 512 can comprise a suitable laser displacement measuring device as known to a person of skill in the art. In one embodiment, the triangulation laser 513 coincides with a spot circle of the laser 502 generated at the target location. The triangulation laser 513 can also be used as a targeting marker when selecting a specific point on the target location 510 as seen with the video camera 516 as the triangulation laser 513 can produce a visible spot on the surface of the target location 510.

The spectrometer 520 collects electromagnetic information from the plume 514. The spectrometer 520 can be a monochromator, a spectrograph or a polychomator. The electromagnetic information includes spectral information identifying an elemental composition of the target location 510. A spectral range for the spectrometer 520 can be chosen to suit different applications. In some embodiments, the spectral range can be approximately 35 nm for observing a portion of the electromagnetic wavelength range. Alternatively, the spectrometer 520 can detect electromagnetic radiation in a range of 200 to 900 nm. Collection optics 522 receive the light and lumina generated from the plume 514 and transmits the light and lumina through a fiber cable 524 to the spectrometer 520. The collection optics 522 can be orientated horizontally. Alternatively, the collection optics 522 can be orientated at any angle above the processed structure 505. A mirror (not shown) within the spectrometer 520 can be used to reflect the lumina to a grating that disperses the lumina.

An intensified charge coupled device (ICCD) or detector 530 is coupled with the spectrometer 520 for detecting the dispersed lumina. The detector 530 provides the detected lumina to the system computer 540. The system computer 540 generates spectral information from the lumina of the laser plume 514. The spectral information includes intensity data representing characteristic information and composition of the target location 510. The spectral information can be produced on a display 542.

The detector 530 provides increased resolution and greater selectivity of the spectral information. The detector 530 can include a microchannel image intensifier plate. The intensifier plate is preferably gated during a period of time when the plume 514 emits characteristic optical emission. This period coincides with an optimum plume luminance period. This period follows emission of continuum radiation. Continuum radiation lacks useful specific species or elemental information. In one embodiment, a delay generator (not shown) can be included to provided gating of the detector 530 to allow temporal resolution of the detector 530 response time. Alternative embodiments of the detector 530 can include a detector other than an ICCD, for example a suitable charge coupled device (CCD) or a suitable photomultiplier. Accuracy of the spectrometer 520 and detector 530 in one embodiment can generate compositional data in the range of 20 ppm or less. Alternatively, the accuracy can be in the range of a few percentage points. In another embodiment, the accuracy can be in the range of 1%.

The system computer 540 can include application software and a controller in the system computer 540 for providing synchronization of the laser 502, spectrometer 520, detector 530, position sensor 512 and the x-y-z motors 508 positioning of the stage 506. The system computer 540 is communicatively coupled with the laser 502, spectrometer 520, detector 530, position sensor 512, the x-y-z motors 508, and the camera 516. The system computer 540 can include a display 542 for displaying spectral information. The system computer 540 can present the spectral data generated on the display 542. Alternatively, a separate personal computer can also be coupled with the system computer 540 for separately analyzing the spectral information. The system computer 540 can include a power controller to regulate power to all the apparatus 500 components.

The application software decodes the spectral information from the detector 530 and facilitates analysis of the spectral information and generates characteristic information of the processed structure 505. In one embodiment, the intensity data of spectral feature is subtracted from background data of the feature to calculate a change in intensity. As previously described, in some embodiments, the present invention can provide feedback to the laser ablation/processing. For example, in some embodiments, as soon as the material from an underlying layer is detected in the laser ablation plume by the optical diagnostics system, the system computer 540 instructs the laser 502 to stop or reduce its power in order to prevent damage to the underlying layer.

The application software allows setting of certain parameters for performing the laser ablations of the target location 510. The size of the laser focus spot circle can be set as a parameter and can be consistently and precisely maintained through the laser ablation process described in further detail below. Alternatively, a z-value for the target location 510 can be set as a parameter and can be consistently and precisely maintained or varied through the laser ablation process. The spot circle increases or decreases depending on the change in height of the target location 510. Keeping the laser 502 spot circle precisely adjusted insures that the target location 510 produces the plume 514 with consistent optimum plume luminance Height changes in the target location can be detected by the position sensor 512 and a correction to the height of the target location 510 is generated by the controller within the system computer 540. The application software and the controller generate correction signals to reposition the height of the stage 506 after each laser ablation of the target location.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A method of manufacture depending on laser ablation, the method comprising:
reconfiguring a surface of a structured solid target by removing material using laser ablation with laser beam pulses emanating from a pulsed laser having a pulse frequency in the range of 0.5 kHz to 1 MHz, pulse energy in the range of microjoule levels to approximately 1 millijoule, and pulse length in the range of at least 10 femtoseconds to hundreds of picoseconds;
selectively recording a plurality of optical emission spectra from the ablated material using temporally resolved spectral data acquisition, wherein each of the optical emission spectra arises from material ablated by a different individual laser pulse,
determining a current chemical composition of material ablated by a current individual laser pulse in real time based on an optical emission spectrum arising from the material ablated by the current individual laser pulse;
detecting at least two different vertical layers in the target and/or at least two different horizontal domains in the target in real time based at least on the current chemical composition; and
performing an action based at least on the current chemical composition;
wherein there is no human interaction and selectively recording each of the optical emission spectra from the material ablated by the respectively different individual laser pulses using temporally resolved spectral data acquisition comprises collecting each of the optical emission spectra exclusively in a time interval between a first preselected delay time after initiation of each individual laser pulse and a longer second preselected delay time after the initiation of each individual laser pulse.

2. The method of claim 1, wherein a plurality of the optical emission spectra arising from material ablated by the different individual laser beam pulses are accumulated in a charge coupled device (CCD) detector chip of a CCD camera and/or of an intensified CCD (ICCD) camera.

3. The method of claim 1, wherein a plurality of the optical emission spectra arising from material ablated by the different individual laser beam pulses are accumulated in a CCD detector chip of an intensified charge coupled device (ICCD) camera wherein the first preselected delay time is less than 1 microsecond.

4. The method of claim 1 wherein each of the optical emission spectra is emitted within a time period shorter than one microsecond following the initiation of each respective ablating laser beam pulse.

5. The method of claim 1 wherein the action is selected from the group consisting of continuing laser pulse ablation, stopping pulsed laser ablation, and changing the amount of pulsed laser beam power being delivered to the substrate.

6. The method of claim 1 further comprising maintaining a focused laser beam spot size of less than one micrometer on a substrate location without human interaction.

7. The method of claim 1 wherein the exclusive collecting of optical emission spectra is performed using a microchannel intensifier plate.

8. The method of claim 1 wherein the first preselected delay time is less than 1 microsecond, each laser beam pulse has a duration in the range of picoseconds to hundreds of picoseconds, and the duration of each optical emission spectrum arising from each individual laser pulse is less than 1 microsecond.

9. The method of claim 1 further comprising maintaining a predetermined focused laser beam spot size in a range of approximately 10 to 500 micrometers on a substrate location without human interaction.

10. The method of claim 9 wherein the different individual laser pulses are consecutive pulses.

11. The method of claim 9 wherein material ablated by a prior laser pulse consists of material from one layer of the substrate, and the material ablated by the current laser pulse includes material from a different layer of the substrate.

12. The method of claim 9 wherein material ablated by a prior laser pulse consists of material from one domain of the substrate, and the material ablated by the current laser includes material from another domain of the substrate.

13. A method of device fabrication depending on laser ablation, the method comprising:
selectively ablating material from a substrate with focused laser beam pulses emanating from a focused pulsed laser having a pulse frequency in the range of 0.5 kHz to 1 MHz, having energy generally in the range of microjoule to millijoule levels per pulse, and pulse length in the range of femtoseconds to hundreds of picoseconds;
selectively acquiring a temporally resolved optical emission spectrum comprising useful spectral features arising from the material ablated by an individual laser pulse during a time interval between different first and second preselected delay times relative to the initiation of the individual laser pulse; and
determining a chemical composition of material ablated by the individual laser beam pulse in real time using the temporally resolved optical emission spectrum arising from the material ablated by the individual laser pulse;
wherein there is continuum emission following each laser pulse and the time interval is after continuum emission.

14. The method of claim 13 wherein the first preselected delay after the initiation and the second preselected delay time after the initiation are optimized to enhance at least one useful spectral feature.

15. The method of claim 13 wherein the first preselected delay after the initiation and the second preselected delay time after the initiation are optimized to decrease a background of continuum emission.

16. The method of claim 13 further comprising performing an action based on the chemical composition, without human interaction.

17. The method of claim 13 further comprising maintaining a focused laser beam spot size of approximately 10 to 500 micrometers on the substrate without human interaction.

18. The method of claim 13 further comprising maintaining a focused laser beam spot size of less than 1 micrometer on the substrate without human interaction.

19. A method of manufacture depending on pulsed laser ablation to selectively remove a substantial amount of material from a solid material surface, the method comprising:
performing the substantial amount of material removal using focused laser beam pulses emanating from a pulsed laser having a frequency in the range of 0.5 kHz to 1 MHz, having energy generally in the range of microjoule to millijoule levels per pulse, and having pulse length in the range of at least 10 femtoseconds to hundreds of picoseconds, whereby a plume of material arising from each laser beam pulse emits characteristic optical radiation;

selectively recording a temporally resolved optical emission spectrum comprising useful spectral features emitted from a plume arising from an individual laser pulse during a time interval between different first and second preselected delay times relative to initiation of the individual pulse; and determining a chemical composition of material ablated by the individual laser beam pulse in real time using the temporally resolved optical emission spectrum arising from the material ablated by the individual pulse;

wherein the plume of material from each laser pulse emits continuum radiation and the preselected delay times are operable to enhance the useful spectral features relative to the continuum radiation.

20. The method of claim 19 further comprising performing an action depending on the current chemical composition, without human interaction.

21. The method of claim 19 wherein the material surface is selected from the group consisting of a surface of a single film, a surface of a multilayered material, a surface of a structured material, and a surface of a material structure.

22. The method of claim 19, further comprising selectively accumulating a plurality of temporally resolved optical emission spectra comprising useful spectral features emitted from the respective plumes of different sequential individual laser pulses in a charge coupled device (CCD) detector chip of a CCD camera and/or of an intensified CCD (ICCD) camera.

23. The method of claim 19, further comprising selectively accumulating a plurality of temporally resolved optical emission spectra comprising useful spectral features emitted from the respective plumes of different sequential individual laser pulses in pixels of a CCD detector chip of an intensified charge coupled device (ICCD) camera during a time interval between different first and second preselected delay times relative to the initiation of the each respective individual pulse, wherein the first preselected delay time is less than 1 microsecond.

24. The method of claim 23 wherein the difference between the second and first preselected delay times is less than 1 microsecond.

* * * * *